United States Patent [19]
Clary

[11] 3,936,733
[45] Feb. 3, 1976

[54] APPARATUS FOR SUPPORTING AN INSPECTION DEVICE FOR TUBULAR MEMBERS AND ACCOMMODATING LATERAL SHIFTING OF THE TUBULAR MEMBERS AS THEY ARE RUN INTO OR PULLED FROM A WELL BORE

[75] Inventor: Derwin R. Clary, Odessa, Tex.
[73] Assignee: Trip Inspectors, Inc., Odessa, Tex.
[22] Filed: Dec. 16, 1974
[21] Appl. No.: 533,322

Related U.S. Application Data
[63] Continuation-in-part of Ser. No. 431,093, Jan. 7, 1974, abandoned.

[52] U.S. Cl. ................................................. 324/37
[51] Int. Cl.² ......................................... G01R 33/12
[58] Field of Search ...................... 324/34 R, 37, 40

[56] References Cited
UNITED STATES PATENTS

| | | | |
|---|---|---|---|
| 3,023,312 | 2/1962 | Wood | 324/37 |
| 3,361,961 | 1/1968 | Zoellick | 324/34 R |
| 3,504,534 | 4/1970 | Mandula, Jr. | 324/37 |
| 3,718,855 | 2/1973 | Rogel et al. | 324/37 |
| 3,736,501 | 5/1973 | Donkin | 324/37 |
| 3,781,663 | 12/1973 | Abarotin et al. | 324/37 |

Primary Examiner—Robert J. Corcoran
Attorney, Agent, or Firm—Jack W. Hayden

[57] ABSTRACT

An arrangement for supporting a tubular inspection unit adjacent a well bore to enable tubular members to be moved through the inspection unit as they are run in or pulled from the well bore to determine characteristics of the tubular members. The arrangement includes an upwardly extending support for positioning adjacent the well bore and a laterally extending arm pivotally secured to the support and being normally positioned, during operation, at a given angular disposition with respect thereto. The pivotal connection allows, at all times, free angular movement of the arm with respect to the support and about a single axis in either angular direction away from the normal position. The arm comprises two members in telescoping relationship and arranged to accommodate, at all times, free axial sliding of one member with respect to the other in directions of both extension and retraction. Thus, the telescoping members of the arm and the pivot allow free movement of the inspection device within a horizontal plane of limited bounds to thereby accommodate lateral shifting of the tubular members as they are run into or pulled from the well bore without affecting operation of the inspection unit.

9 Claims, 10 Drawing Figures

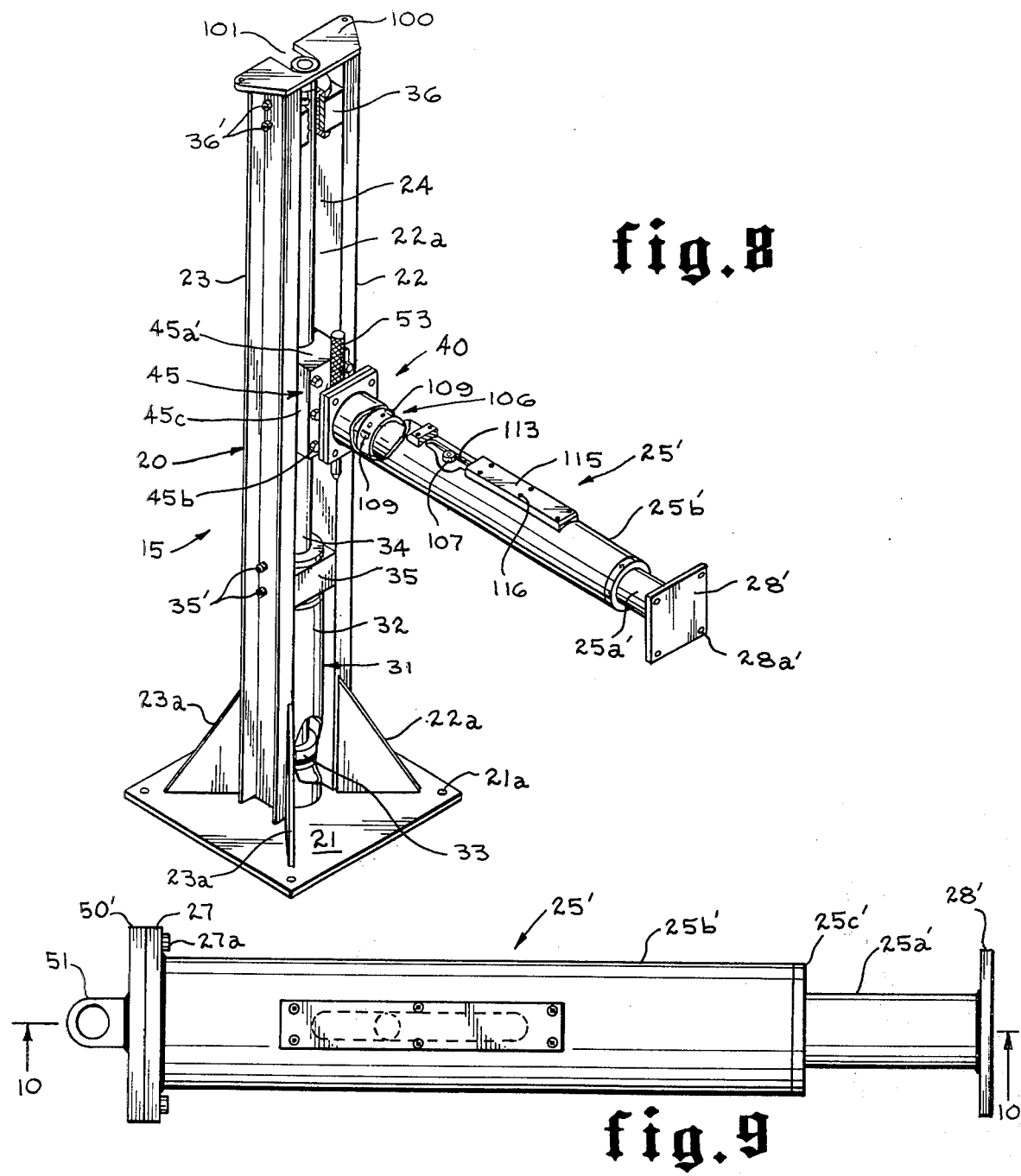
fig. 8
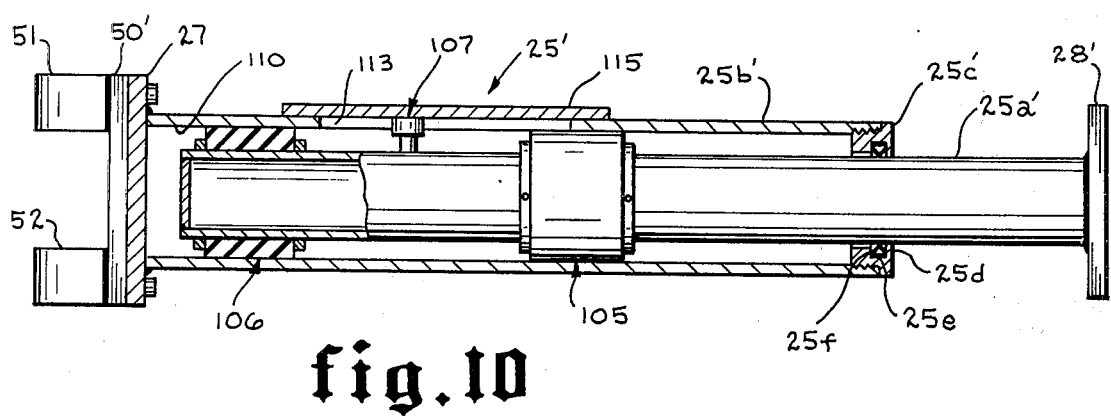
fig. 9
fig. 10

APPARATUS FOR SUPPORTING AN INSPECTION DEVICE FOR TUBULAR MEMBERS AND ACCOMMODATING LATERAL SHIFTING OF THE TUBULAR MEMBERS AS THEY ARE RUN INTO OR PULLED FROM A WELL BORE

CROSS REFERENCE TO RELATED APPLICATION

This application is a continuation-in-part of my prior copending application Ser. No. 431,093, filed Jan. 7, 1974 for "Method And Apparatus For Inspecting Tubular Members As They Are Run Into Or Pulled From A Well Bore", now abandoned. The present applicatoin may be employed for supporting the invention disclosed in my copending application Ser. No. 431,125, filed on Jan. 7, 1974 for "Gage For Tubular Members".

SUMMARY OF THE INVENTION

The present invention provides a method and support arrangement for inspecting tubular members as they are run in or withdrawn from a well bore. The support arrangement positions the inspection head preferably immediately adjacent the rotary table, when a rotary table is employed, and enables the inspection unit to be moved away from the rotary table either in the event of an emergency, or for other reasons during running or pulling of tubular members, such as to enable the slips to be set in the rotary table in a manner well known in the art.

The support arrangement is adaptable to accommodate lateral shifting of the tubular members as they are moved into or removed from the well bore without affecting the operation of the inspection unit.

An object of the present invention is to provide a relative simple arrangement to support a device adjacent a well bore to enable tubular members run in or pulled from the well bore to be moved through the device to be inspected for defects.

Yet a further object of the present invention is to provide a relatively simple support arrangement for an inspection unit including an electromagnetic induction device and a gage for measuring variations in the outside diameter of tubular members as they are run in or pulled from a well bore.

Still another object of the present invention is to provide a support arrangement for an inspection unit adjacent a well bore so that as the tubular members are run in or pulled from the well bore, they may be simultaneously rotated and inspected for defects.

Still another object of the present invention is to provide a method of inspecting tubular members as they are run in or pulled from a well bore which accomplishes such inspection without interference from tool joints, couplings, rubber protectors and the like.

An object of the present invention is to provide a relative simple arrangement to support a device adjacent a well bore to enable tubular members run in or pulled from the well bore to be moved through the device to be inspected to defects and wherein the arrangement enables the device to shift in response to shifting of the tubular members as they are moved through the device.

Other objects and advantages of the present invention will become apparent from a consideration of the following description and drawings.

BRIEF DESCRIPTION OF THE DRAWINGS

FIG. 8 is a perspective view of another form of the invention;

FIG. 9 is a plan view of part of the structure shown in FIG. 8; and

FIG. 10 is a plan view on the line 10—10 of FIG. 9, partly in section.

DESCRIPTION OF THE PREFERRED EMBODIMENT

Figure 1:
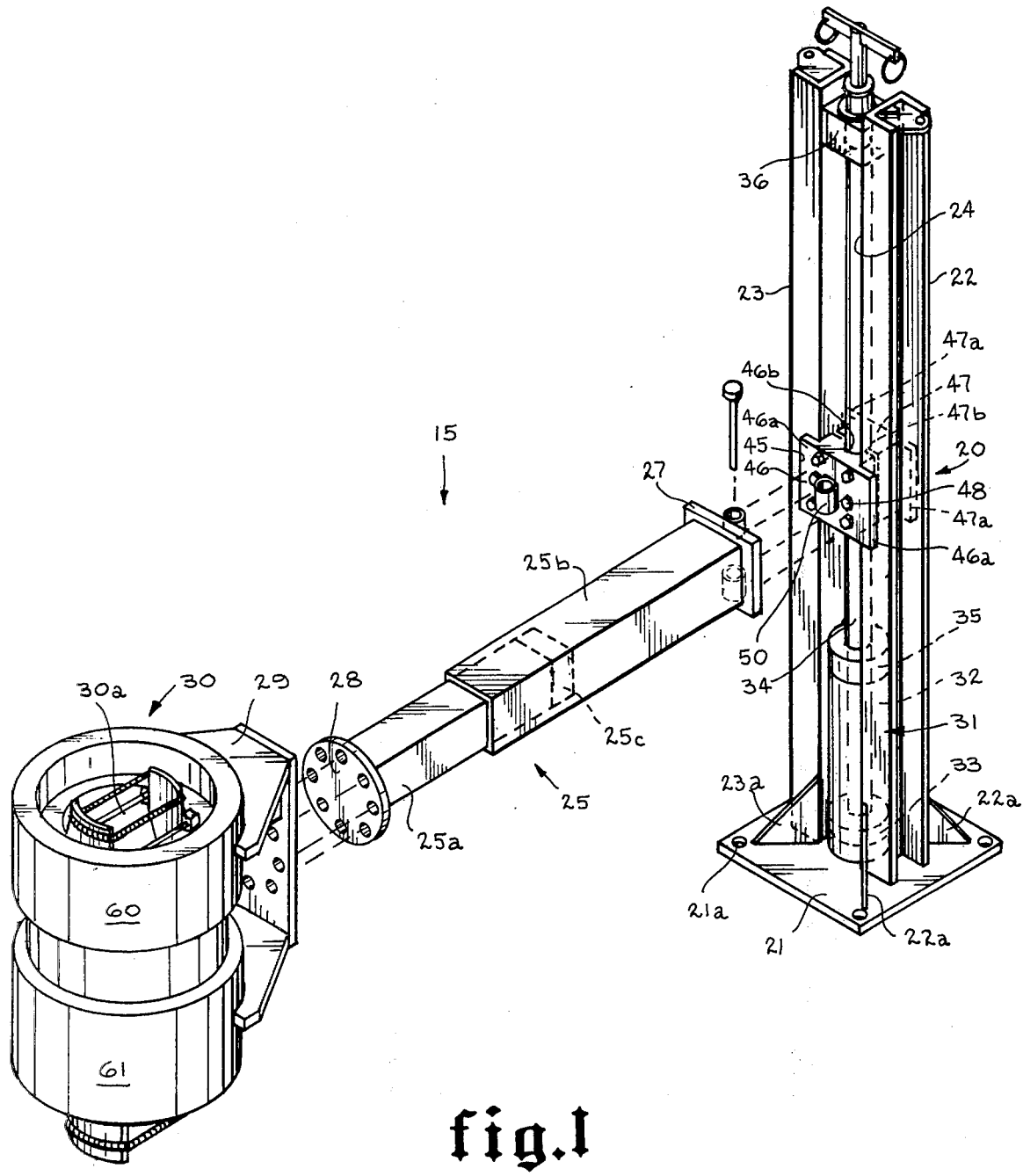
FIG. 1 is a partially exploded, isometric view of a form of the present invention.

Attention is first directed to FIG. 1 of the drawings wherein the invention is referred to generally by the numeral 15. An upwardly extending support arrangement referred to generally at 20 is provied for receiving the laterally extending arm means referred to generally at 25. The inspection unit referred to generally at 30 is supported on the laterally extending arm means 25, and is provided with an aperture 30a for receiving tubular members therethrough. As is readily apparent from the drawings, the inspection unit 30 surrounds and defines central aperture 30a.

The upwardly extending support 20 includes a base 21 which may be provided with openings such as illustrated at 21a for receiving suitable means such as bolts for securing the support 20 upright in position on a drilling rig floor or the like. The upwardly extending support 20 is shown as also including the spaced members 22 and 23 defining a longitudinally extending recess 24 therebetween.

As shown the members 22 and 23 are formed of channels, each including a base or web and two side portions and each member 22, 23 may be secured to the base 21 by any suitable means such as the supports 22a and 23a which may be welded between the base 21 and the respective member 22 and 23.

Positioned in the longitudinally extending recess 24 is suitable power means referred to generally at 31 and as shown such power means includes a cylinder 32 resting or secured to base 21 with piston means 33 therein which piston means 33 is secured to shaft means 34 extending longitudinally between the members 22 and 23 within the space 24. Suitable spaced bearing means referred to at 35 and 36 carried between the members 22 and 23 provides support for the shaft means 34 and aids in guiding the shaft means 34 during movement thereof as will be described.

The laterally extending arm 25 is shown as including at least two members 25a and 25b arranged in telescoping relationship. As illustrated, the members 25a and 25b are non-circular in configuration; however, they could be of any other desired configuration. Suitable bearing means 25c are provided between the telescopic members 25a and 25b to accommodate, at all times, free telescopic movement therebetween.

Figure 2:
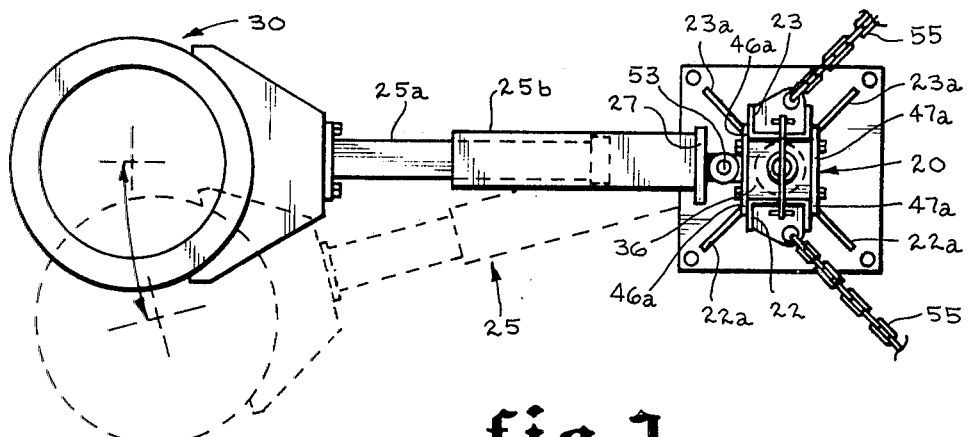
FIG. 2 is a top plan view of the form of the invention illustrated in FIG. 1.

The laterally extending arm means 25 is adapted to be secured to the upwardly extending support 20 by any suitable means and as shown is pivotally connected by the arrangement generally referred to at 40 to enable the laterally extending arm means 25 to swing in a plane generally horizontal relative to the upwardly extending upright 20 as illustrated in dotted line in FIG. 2 of the drawing.

Suitable clamp means referred to generally at 45 comprising the blocks 46 and 47 are provided for fitting in space 24 and engaging with the shaft means 34. The two blocks 46 and 47 are each provided with overlapping edge portions 46a and 47a and each is provided with a partial circular opening as shown at 46b and 47b so that when the two blocks are positioned in the opening 24 as shown in FIG. 1 of the drawings, they will fit about the shaft means 34 and thereafter nut and bolt means 48 may be secured through the blocks 46 to clamp them in position on the shaft 34 in the opening 24.

Figure 3:
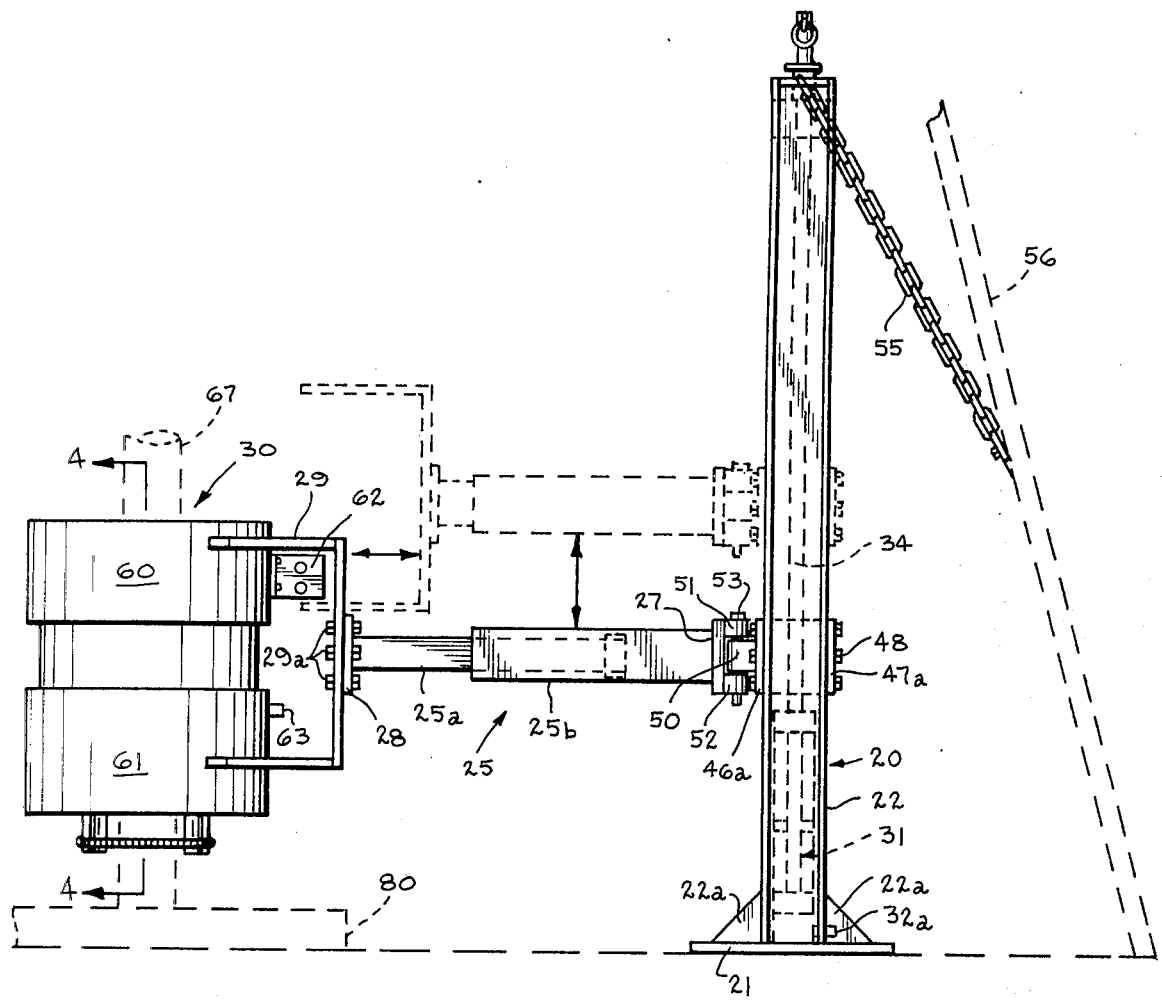
FIG. 3 is a side view of the form of the invention shown in FIG. 1 and illustrates in dotted line an alternate position of a portion of the support means as well as an arrangement for securing an upwardly extending support member in position on a drilling rig.

When the blocks 46 and 47 are clamped in position on the shaft 34, their overlapping edge portions 46a and 47a respectively engage the members 22 and 23 as illustrated in FIGS. 1, 2 and 3 of the drawings to act as guide means during movement of the shaft means 34 when the power means 31 is actuated.

The block 46 is also provided with the circular socket 50 which fits between the spaced circular sockets 51 and 52 mounted on the end 27 of the laterally extending arm means 25. Such spaced socket means 51 and 52 when aligned with the socket 50 are adapted to receive the pin means 53 therein so as to pivotally support the laterally extending arm means 25 in position on the upwardly extending support 20.

As shown in FIGS. 2 and 3, additional support for the upwardly extending support 20 may be provided in the form of chains 55 secured to each side thereof and extending to an adjacent leg of a drilling rig, or stationary power component illustrated by the dotted line at 56 in FIG. 3 of the drawing.

The end 28 of the laterally extending arm means 25 is adapted to be engaged with the bracket 29 which is shown as secured to the inspection unit 30 so that in turn the end 28 and bracket 29 may be secured together by nut and bolts 29a.

The inspection unit 30 as illustrated in FIGS. 1 thru 6 includes a gage 60 for measuring variations in the outside diameter of tubular members moved through the inspection unit 30, the details of such outside diameter gage being described and claimed in my copending application filed on the 7th day of Jan., 1974 and bearing U.S. Ser. No. 431,125 and entitled "Gage FOR TUBULAR MEMBERS".

The inspection unit 30 in FIGS. 1 thru 6 is also shown as including an electromagnetic induction inspection unit 61 to aid in determining any defects, flaws, pits or fatigue cracks both internally and externally of tubular members which are moved longitudinally through the inspection unit 30.

As shown in FIG. 3, suitable power means for rotating the outside diameter gage 60 is provided and is illustrated as being a fluid motor 62 or the like which motor is provided with suitable means for receiving power from a source (not shown) which may be located at any position in the vicinity of the unit.

Similarly, the electromagnetic inspection unit 61 is provided with means 63 for receiving power from a suitable power source to supply power to the inspection unit and to operate the electromagnetic induction inspection unit in a manner well known in the art.

Figure 4:
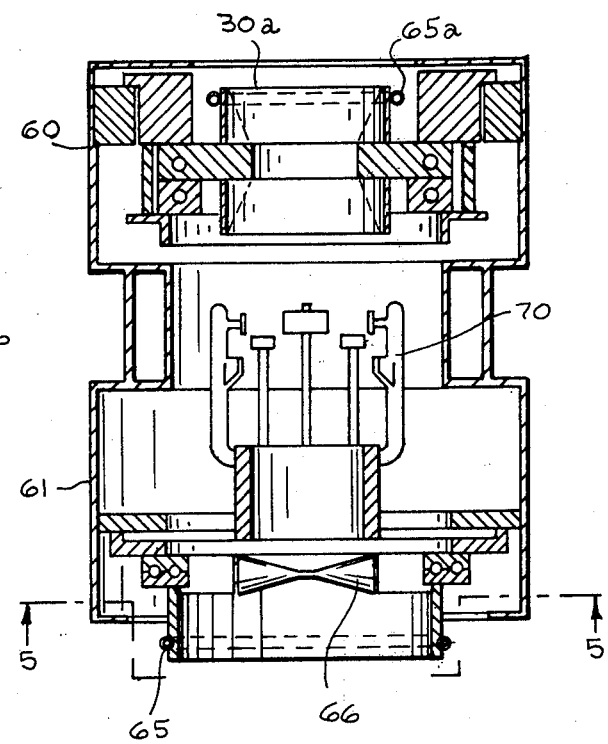
FIG. 4 is a sectional view on the line 4—4 of FIG. 3 and generally diagrammatically illustrating the arrangement of the outside diameter gage and the electromagnetic induction inspection device forming the inspecting unit.

In FIG. 4, the outside diameter pipe gage 60 is shown in schematic detail as is the electromagnetic inspection unit 61. Suitable means such as the spring arrangement 65 is provided for urging the rollers 66 into continuous engagment with a tubular member as illustrated at 67 in FIG. 5, which rollers are in turn mounted by means well known in the art with the inspection shoes referred to generally at 70.

Figure 6:
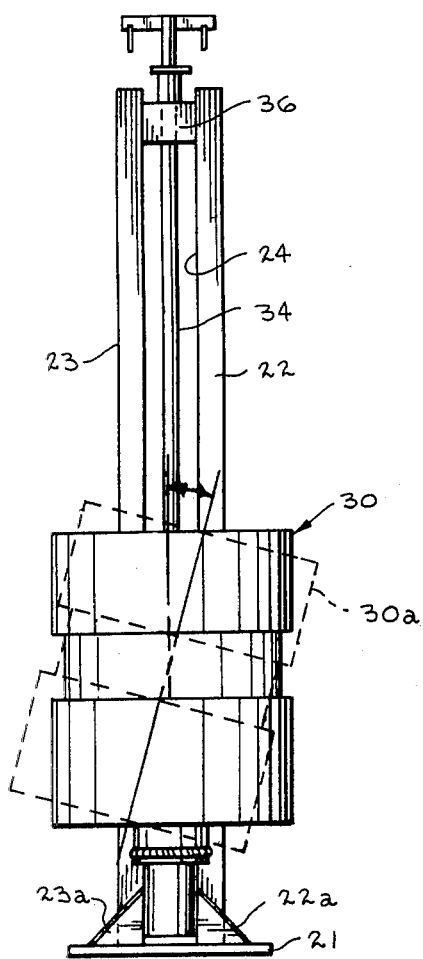
FIG. 6 is an end view of the device illustrating in dotted line a tilted position of the inspection unit.
Figure 5:
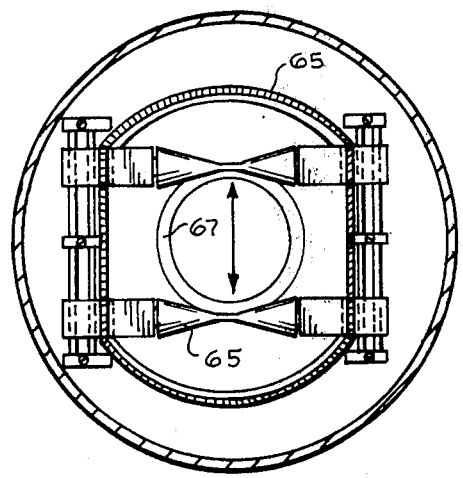
FIG. 5 is a sectional view on the line 5—5 of FIG. 4 to better illustrate an arrangement for continuously engaging the tubular members with the electromagnetic induction inspection part of the testing unit.

As is shown in FIG. 6 of the drawings, the circular configuration of the end of the bracket 29 and the end 28 of the laterally extending arm is such that the inspection unit may be positioned at any desired angle relative to the vertical should such become necessary merely by rotating the inspection unit 30 relative to bracket 28 as illustrated in dotted line at 30a of FIG. 6, and then securing nuts and bolts 29a in position in each.

In FIG. 3 of the drawings, a rotary table commomly employed on an oil and gas drilling rig is illustrated in dotted line at 80, and during normal operation of the present invention it is desired to have the inspection unit 30 in close proximity to such rotary table as shown in FIG. 3 of the drawings. During such time, the tubular member represented in dotted line at 67 is either being run into or pulled from the well bore immediately therebeneath and aligned with the aperture in the inspection unit 30.

Should it become desirable to set slips in the rotary table while either running or pulling the tubular members, or should it become desirable to move the inspection unit vertically relative to the rotary table 80 for any other reason, suitable fluid power may be supplied to the cylinder 32 through the connection 32a to act on the piston 33 and move the shaft 34 upwardly in the space 24 between the members 22 and 23. When this occurs, the laterally extending arm means 25 will also move upwardly since it is clamped therewith by means of the blocks 46 and 47.

The inspection unit 30 may then be lowered back into position when desired by releasing the fluid from cylinder 33.

Also, as previously mentioned and as illustrated in FIG. 2 of the drawings the inspection unit 30 and laterally extending arm means 25 may be swung in a horizontal plane relative to the upwardly extending support 20 as shown in dotted line in FIG. 2 by means of the pivot arrangement 40. The solid line position of FIG. 2 may be considered the normal position and the dotted line position an angularly spaced position. It is clear from the foregoing and from the drawing that the pivot arrangement 40 allows, at all times, free pivotal movement of the laterally extending arm means 25 with respect to the support and about a single axis in either angular direction away from the normal position.

Figure 7:
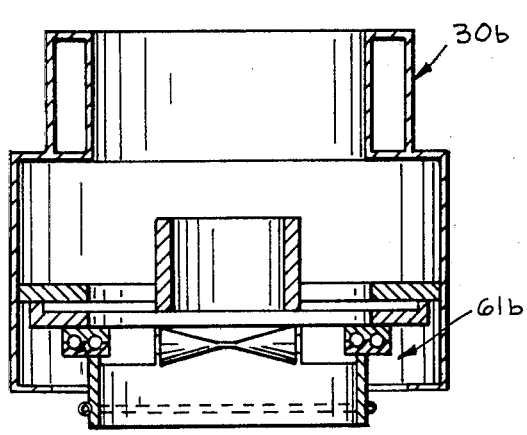
FIG. 7 is a sectional view somewhat similar to FIG. 4 and showing only an electromagnetic induction inspection unit.

In FIG. 7, an arrangement of an inspection unit referred to generally at 30b is shown wherein only an electromagnetic induction inspection unit referred to at 61b is employed.

In FIGS. 8, 9 and 10, an alternate form of the invention 15 is illustrated wherein like numerals are employed to designate like parts as shown in FIGS. 1–7.

The base 21 is provided with openings 21a for securing the invention 15 in position to use. The spaced members 22 and 23 form the longitudinal recess 24 therebetween, and the power means 31 is positioned on the base 21 at the lower end of the recess 24.

The power means includes cylinder 32 with piston 33 therein and shaft 34 connected to piston 33 and extending upwardly in the recess 24 between members 22 and 23 as shown. Suitable spaced bearing means 35 and 36 guide and support shaft 34 when is moves.

Suitable grease connections 35' and 36' are provided on member 23 for supplying grease to the bearing means 35 and 36 respectively.

The upper end of members 22 and 23 is provided with a plate 100 secured thereto having groove or opening 101 therein to enable the shaft to be moved readily and positioned between members 22 and 23.

The arm 25' is pivotally connected by the arrangement generally referred to at 40 to the upwardly extending support arrangement 20 in the manner as described with regard to FIGS. 1–7. Such pivotal support arrangement includes the spaced socket means 51 and 52 carried on plate 50' which in turn is secured by any suitable means such as the nuts 27a which extend through the end 27 of the arm 25' and engage with the plate 50'. A socket 50 (not shown) is carried by the clamp arrangement referred to generally at 45 and fits between the socket means 51 and 52 whereupon a suitable pin or threaded member 53 may be engaged therewith to secure the arm 25' pivotally with the clamp arrangement 25 that engages the shaft or piston rod 34.

In this form of the invention the clamp arrangement 45 comprises a block 45a which may be formed of two members having a semicylindrical mating void extending longitudinally therethrough for fitting about the shaft 34. The two block portions may be secured together about and on shaft 34 by any suitable means such as the bolts 45b extending therethrough. The sides 45c of the blocks slidably engage the web 22a and 23a of the members 22 and 23 upon movement of the piston rod 34.

In this form of the invention it will be noted that the laterally extending arm means 25 is shown as being cylindrical in configuration and includes the two members 25a' and 25b' which are arranged in telescoping relationship. The end 28' of the support 25', which end 28 is in the form of a rectangular plate having openings 28a' therein for receiving and supporting the inspection unit 30 as described with regard to FIGS. 1–7 inclusive.

The cylindrical member 25b' is provided with a closure 25c which is adapted to be threadedly secured with the end of 25b' as shown, such closure having an opening 25d therethrough with an annular groove 25e therein for receiving the seal means 25f which sealingly and slidably engages the member 25a'.

Suitable bearing means represented generally at 105 and 106 are provided on the arm or member 25a' to aid in guiding the arm 25a' upon relative longitudinal movement within the arm or member 25b'. Additional bearing means referred to generally at 107 positioned between the bearing means 105 and 106 are provided for further guiding the member 25a' as it moves longitudinally of the member 25b'. As shown in FIG. 8, the bearing means 106 includes a plurality of circumferentially spaced roller means 109 carried by the bearing 106 which engage the inner surface 110 of the arm or member 25b' as movement between 25a' and 25b' occurs. The bearing means 105 may be a sleeve bearing as shown.

The bearing means 107 rotatably fits within a groove 113 formed in the member 25b'.

As more clearly shown in FIG. 8, the groove 113 is partially cut away so that the relationship of the bearing means 107 to such groove in the arm 25b' is more clearly visible and understood. The groove or slot 113 limits the relative longitudinal movement of member 25a' and 25b' and also inhibits relative rotation therebetween.

A suitable cover plate as shown at 115 may be secured to the arm 25b' by any suitable means such as screws 116 or the like for access to the bearing means 107 for replacement or repair as may be necessary.

A suitable connection is provided to the cylinder 32 for supplying fluid to such cylinder to position the laterally extending arm 25 in any desired vertical relationship in a manner as described with regard to FIGS. 1–7. The function and operation of the support means is similar to that described with regard to FIGS. 1–7 in that the pivotal arrangement 40 enables the support arrangement and whatever device may be carried thereby to be shifted in a vertical plane by reason of the power means 31.

Relative longitudinal movement between the members 25a' and 25b' may occur as may be necessary during use of the invention.

In the operation of the present invention, it is positioned in relation to the rotary table 80 so as to receive tubular members therethrough either as they are lowered, or run into the well bore, or as the tubular members are step wise pulled from the well bore as represented in FIG. 3 of the drawings. At any event, the outside diameter gage is rotated as described in my copending application hereinabove referred to. Simultaneously suitable power is supplied to the electromagnetic induction inspection unit 61 so as to power it and induce a magnetic field within the tubular member as it passes through the inspection unit 30.

The outside diameter gage 60 of the inspection unit 30 measures any variations in diameter of the tubular members passing therethrough, and the inspection shoes 70 of the electromagnetic induction inspection unit ride on the tubular members and detect any anomaly in the induced magnetic field as an indication of corrosion pits, fatigue cracks or other defects externally and internally in the tubular member.

The spring arrangement 65 accommodates the movement of couplings, tool joints and protectors through the electromagnetic inspection unit 61 and the spring arrangement 65a on the outside diameter gage also does the same thing.

The construction and arrangement and method of use for the present invention provides a minimum inference with normal crew activity involved in running or pulling tubular members on an oil or gas rig, or with other crew activity that may be under way on the drilling rig.

The operation of the inspection unit is not affected by tool joints, couplings, and/or protectors and it can be appreciated that the inspection scans a full 360° of the tubular members either as they are run in or pulled from the well bore.

The foregoing invention not only provides a simple arrangement for testing tubular members, but enables a method of testing tubular members to determine any defects or wear therein that might cause problems during drilling of the well or during subsequent production operations.

The foregoing disclosure and description of the invention is illustrative and explanatory thereof, and various changes in the size, shape, and materials as well as in the details of the illustrated construction may be made without departing from the spirit of the invention.

What is claimed is:

1. An arrangement for supporting an inspection device adjacent a well bore for moving tubular members through the inspection device as they are run into or pulled from the well bore including:
   a. an upwardly extending support for positioning adjacent a well bore;
   b. laterally extending arm means secured to said upwardly extending support and being normally positioned, during operation, at a given angular disposition with respect thereto;
   c. a single pivot means between said upwardly extending support and said laterally extending arm means for allowing, at all times, free pivotal movement of said arm means with respect to said support and about a single axis in either angular direction away from said normal position;
   d. said arm means comprising two members in telescoping relationship and arranged to accommodate, at all times, free axial sliding of one member with respect to the other in directions of both extension and retraction;
   e. bearing means between said two members to facilitate said free axial sliding and to guide and support said members;
   f. a device for inspecting tubular members, said inspection device surrounding a central aperture defined by said inspection device and through which tubular members may pass, said inspection device being carried by said arm means; whereby said telescoping members of said arm and said pivot means allow free movement of said inspection device within a plane of limited bounds to accommodate lateral shifting of tubular members as they are run into or pulled from the well bore without affecting operation of the inspection device.

2. The invention of claim 1 wherein said upwardly extending support includes means for positioning said laterally extending arm at predetermined longitudinal positions on said upwardly extending support.

3. The invention of claim 1 including bracket means mounted on said laterally extending arm and engaged with said device.

4. The invention of claim 2 wherein said positioning means includes:
   a. power means;
   b. shaft means movable by said power means;
   c. clamp means for securing to said shaft means and including guide means for slidably engaging siad upwardly extending support; and
   d. means for securing said laterally extending arm means to said clamp means.

5. The invention of claim 4 wherein said power means includes cylinder means with piston means therein, and wherein said piston means is connected to said shaft means.

6. The invention of claim 5 including bearing means at spaced intervals in said upwardly extending support and engaging said shaft means.

7. The invention of claim 1 wherein said bearing means includes a pair of spaced bearing means carried by one of said telescoping members for engaging the interior of the other of said telescoping members.

8. The invention of claim 7 wherein at least one of said bearing means includes roller means for engaging the interior of the other of said telescoping members.

9. The invention of claim 1 wherein said bearing means includes:
   a. a slot in one of said members; and
   b. rotatable bearing means mounted on the other of said members and engaged in said slot.

* * * * *